US009316746B2

(12) United States Patent
Nishino et al.

(10) Patent No.: US 9,316,746 B2
(45) Date of Patent: Apr. 19, 2016

(54) RADIOGRAPHY SYSTEM AND RADIOGRAPHY METHOD

(71) Applicant: FUJIFILM Corporation, Tokyo (JP)

(72) Inventors: Naoyuki Nishino, Ashigarakami-gun (JP); Yasunori Ohta, Ashigarakami-gun (JP); Haruyasu Nakatsugawa, Ashigarakami-gun (JP); Kouichi Kitano, Ashigarakami-gun (JP); Naoto Iwakiri, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 9 days.

(21) Appl. No.: 14/228,638

(22) Filed: Mar. 28, 2014

(65) Prior Publication Data

US 2014/0209806 A1    Jul. 31, 2014

Related U.S. Application Data

(63) Continuation of application No. PCT/JP2012/068321, filed on Jul. 19, 2012.

(30) Foreign Application Priority Data

Sep. 29, 2011    (JP) .................................. 2011-214547

(51) Int. Cl.
  *G01T 1/17* (2006.01)
  *G06K 9/36* (2006.01)
  *H05G 1/58* (2006.01)
  *H05G 1/60* (2006.01)
  *A61B 6/00* (2006.01)

(52) U.S. Cl.
  CPC ................ *G01T 1/17* (2013.01); *A61B 6/4007* (2013.01)

(58) Field of Classification Search
  CPC .......... G06K 9/20; G01T 1/17; A61B 6/4007; A61B 6/4014; A61B 6/507; H05G 1/58; H05G 1/60; H05G 1/70
  See application file for complete search history.

(56) References Cited

U.S. PATENT DOCUMENTS

| 7,381,963 | B2 * | 6/2008 | Endo ..................... G01T 1/2018 250/370.09 |
| 7,994,481 | B2 * | 8/2011 | Yagi et al. ................ 250/370.09 |
| 2009/0316860 | A1 | 12/2009 | Okunuki et al. |
| 2011/0049378 | A1 * | 3/2011 | Omura ................... G03B 42/04 250/370.15 |
| 2011/0216884 | A1 | 9/2011 | Tsujii et al. |
| 2012/0106702 | A1 * | 5/2012 | Feke .................... A61B 5/0059 378/63 |

FOREIGN PATENT DOCUMENTS

| JP | 2007-265981 A | 10/2007 |
| JP | 2010-115270 A | 5/2010 |

OTHER PUBLICATIONS

International Search Report for PCT/JP2012/068321 dated Aug. 21, 2012.

* cited by examiner

*Primary Examiner* — David Porta
*Assistant Examiner* — Faye Boosalis
(74) *Attorney, Agent, or Firm* — Birch, Stewart, Kolasch & Birch, LLP

(57) ABSTRACT

The present invention pertains to a radiography system and a radiography method. A radiation output device has a plurality of radiation sources disposed along a predetermined plane. Also, in accordance with whether an imaging state is a still image mode or a moving picture mode, at least one of the radiation sources that outputs radiation among the plurality of radiation sources is selected.

13 Claims, 12 Drawing Sheets

| a | b | c | d |
| e | f | g | h |
| i | j | k | l |
| m | n | o | p |

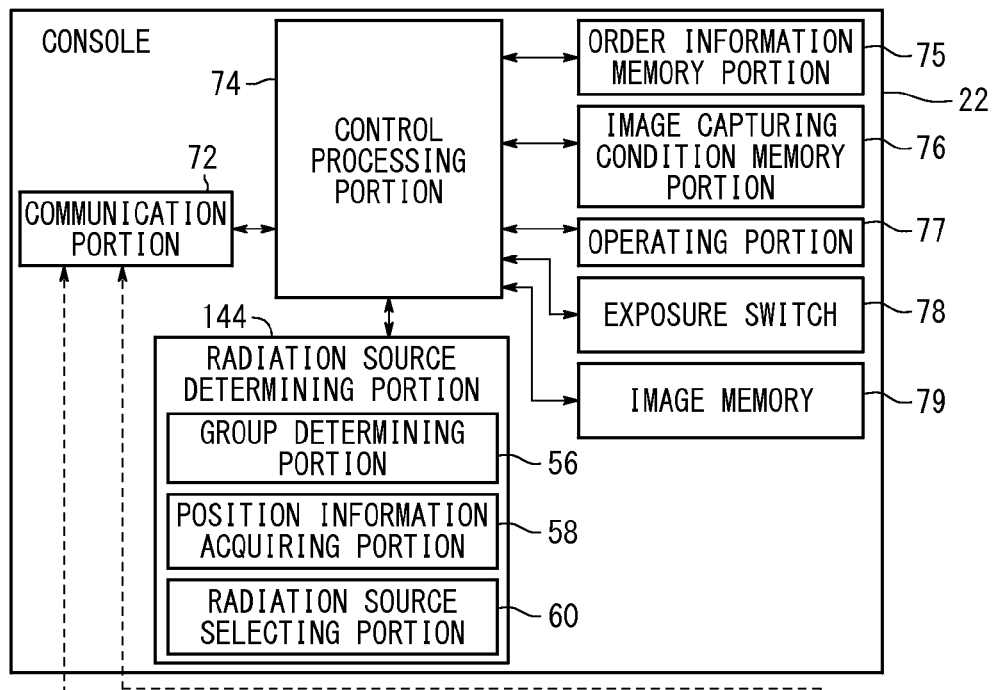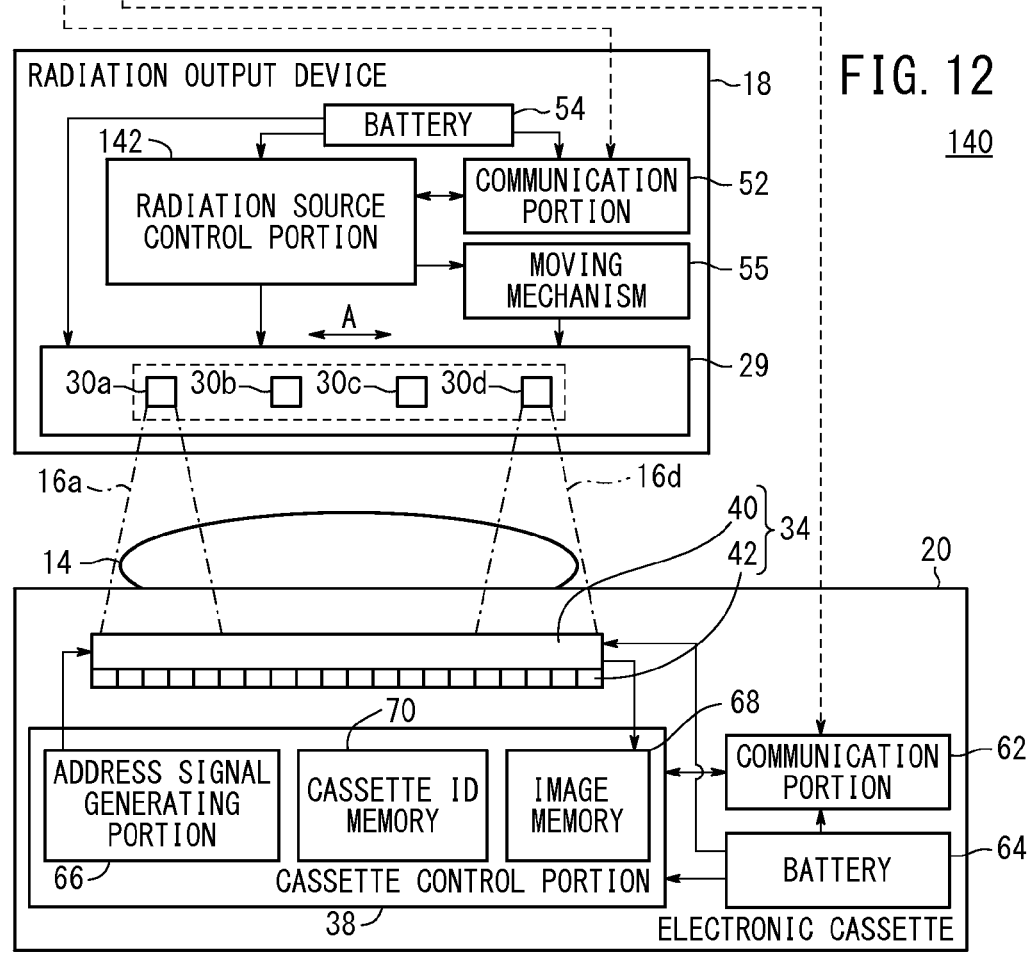
FIG. 12

RADIOGRAPHY SYSTEM AND RADIOGRAPHY METHOD

CROSS-REFERENCE TO RELATED APPLICATIONS AND PRIORITY CLAIM

This application is a Continuation of International Application No. PCT/JP2012/068321 filed on Jul. 19, 2012, which was published under PCT Article 21(2) in Japanese, which is based upon and claims the benefit of priority from Japanese Patent Application No. 2011-214547 filed on Sep. 29, 2011, the contents all of which are incorporated herein by reference.

TECHNICAL FIELD

The present invention relates to a radiographic image capturing system and a radiographic image capturing method (radiography system and radiography method) using a radiation output device having a plurality of radiation sources arranged along a predetermined surface.

BACKGROUND ART

Recently, a variety of radiation output devices have been proposed that incorporate plural radiation sources arranged along a predetermined surface. Various radiographic image capturing methods using such radiation output devices have also been proposed.

Japanese Laid-Open Patent Publication No. 2010-115270 states that an observational area can be changed, e.g., scaled up and down, by controlling the size and position of a collimator in a fluoroscopy (moving image capturing) technique.

SUMMARY OF INVENTION

Radiographic image capturing processes are roughly classified into two image capturing modes depending on whether a temporal element is involved or not. More specifically, one image capturing mode is defined by a still image mode for capturing a radiographic image in a single image capturing event, and another image capturing mode is defined by a moving image mode for capturing a succession of radiographic images in successive image capturing events. Japanese Laid-Open Patent Publication No. 2010-115270 makes no specific proposals in relation to performing a radiographic image capturing process using both a still image mode and a moving image mode. Therefore, an unsolved problem remains as to how a plurality of radiation sources should be used.

The present invention has been made in view of the aforementioned problem. It is an object of the present invention to provide a radiographic image capturing system and a radiographic image capturing method, which are capable of greatly increasing the efficiency with which an operator is able to work in carrying out a radiographic image capturing process using both a still image mode and a moving image mode.

According to the present invention, there is provided a radiographic image capturing system comprising a radiation output device having a plurality of radiation sources arranged along a predetermined surface, and an output control portion for controlling emissions of radiation, respectively, from the radiation sources of the radiation output device, wherein the output control portion includes a radiation source selecting portion for selecting at least one of the radiation sources for emitting the radiation depending on whether an image capturing mode is a still image mode or a moving image mode.

Since the output control portion selects at least one of the radiation sources for emitting radiation depending on whether the image capturing mode is a still image mode or a moving image mode, it is possible to emit radiation from a position suitable for the image capturing mode, without the need for moving the radiation sources and positioning the subject differently. Consequently, the efficiency with which an operator works in capturing images in the still image mode and the moving image mode is greatly increased.

Preferably, the predetermined surface comprises a planar surface, and the radiation sources are arranged in a matrix.

Preferably, the output control portion further includes a group determining portion for determining a first radiation source group to be used in the still image mode from among the radiation sources, and the radiation source selecting portion selects at least one of the radiation sources from among the first radiation source group determined by the group determining portion in a case where the image capturing mode is the still image mode. Consequently, it is possible to emit radiation from at least one position, which is suitable for a radiographic image capturing process in the still image mode.

Preferably, the group determining portion determines a second radiation source group to be used in the moving image mode from among the radiation sources, and the radiation source selecting portion selects at least one of the radiation sources from among the second radiation source group determined by the group determining portion in a case where the image capturing mode is the moving image mode. Consequently, it is possible to emit radiation from at least one position, which is suitable for a radiographic image capturing process in the moving image mode.

Preferably, the group determining portion determines the first radiation source group and the second radiation source group such that each of the radiation sources belongs to either one of the first radiation source group and the second radiation source group.

Preferably, the radiation source selecting portion selects at least one of the radiation sources depending on a positional relationship between a region of interest of a subject as a target to be imaged and each of the radiation sources. Consequently, it is possible to perform a radiographic image capturing process that is suitable for the region of interest, regardless of whether the image capturing mode is the still image mode or the moving image mode.

Preferably, in the case where the image capturing mode is the still image mode, the radiation source selecting portion selects at least one of the radiation sources, which resides at a position located a short distance with respect to the region of interest.

Preferably, in the case where the image capturing mode is the still image mode, the radiation source selecting portion selects at least one of the radiation sources, which resides at a position having a small irradiation angle with respect to the region of interest.

Preferably, the radiation source selecting portion selects a cluster of at least two of the radiation sources, as the predetermined surface is viewed in plan. In this manner, the respective emissions of radiation, which are emitted simultaneously from the selected radiation sources, are closely bundled, so as to prevent a resultant radiographic image from suffering from geometric distortions.

Preferably, the output control portion successively controls the emissions of radiation depending on the still image mode at longer time intervals than a frame interval of the moving image mode. Consequently, images can reliably be captured in the still image mode without a loss in timing, even though states of the target to be imaged (characteristics of the radiographic images) are changed from time to time.

Preferably, the radiographic image capturing system further comprises a moving mechanism for moving the radiation sources in unison with each other.

Preferably, the radiographic image capturing system further comprises a radiographic image capturing apparatus for converting the radiation emitted respectively from the radiation sources into a radiographic image.

According to the present invention, there also is provided a radiographic image capturing method using a radiation output device having a plurality of radiation sources arranged along a predetermined surface, comprising the step of selecting at least one of the radiation sources for emitting radiation from among the plurality of radiation sources of the radiation output device, depending on whether an image capturing mode is a still image mode or a moving image mode.

With the radiographic image capturing system and the radiographic image capturing method according to the present invention, inasmuch as at least one radiation source for emitting radiation is selected from among the plural radiation sources depending on whether the image capturing mode is the still image mode or the moving image mode, it is possible to emit radiation from a position that is suitable for the image capturing mode, without the need for moving the radiation sources and positioning the subject differently. Consequently, the efficiency with which an operator works in capturing images in the still image mode and the moving image mode is significantly increased.

BRIEF DESCRIPTION OF DRAWINGS

FIG. 12 is an electric block diagram of a radiographic image capturing system according to a second modification.

DESCRIPTION OF EMBODIMENTS

A radiographic image capturing method according to a preferred embodiment of the present invention, which is carried out by way of a radiographic image capturing system, will be described below with reference to the accompanying drawings.

[Arrangement of Radiographic Image Capturing System 10]

Figure 1:
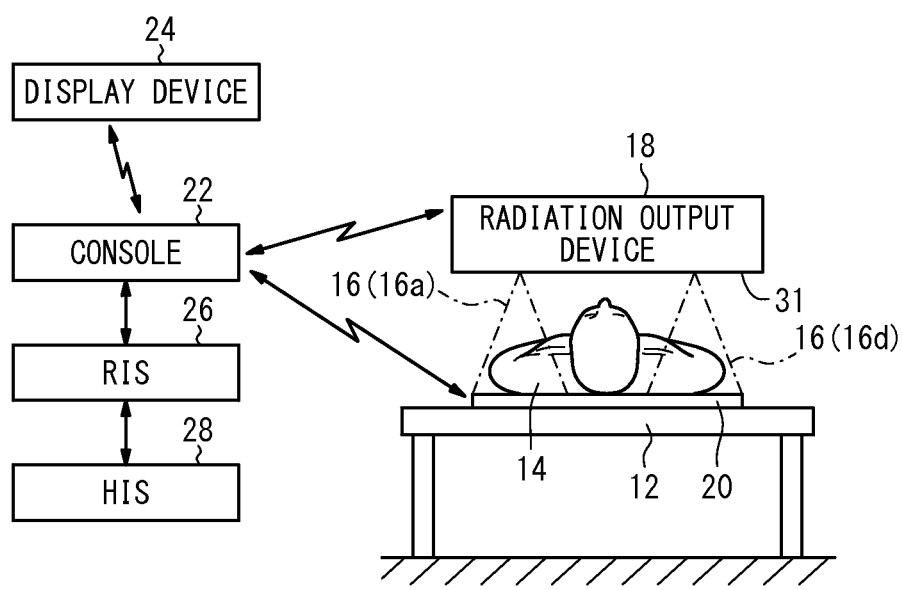
FIG. 1 is a diagram of a radiographic image capturing system according to an embodiment of the present invention.

As shown in FIG. 1, a radiographic image capturing system 10 includes a radiation output device 18 for applying radiation 16 to a patient as a subject 14 lying on an image capturing table 12 such as a bed or the like, an electronic cassette 20 for detecting radiation 16 that has passed through the subject 14 and converting the detected radiation 16 into a radiographic image, a console 22 for controlling the radiation output device 18 and the electronic cassette 20, and a display device 24 for displaying the radiographic image.

The console 22, the radiation output device 18, the electronic cassette 20, and the display device 24 send signals to and receive signals from each other via UWB (Ultra Wide Band) communications, over a wireless LAN (Local Area Network) according to standards such as IEEE 802.11.a/b/g/n, or by way of millimeter-wave communications. Alternatively, such signals may be sent and received mutually via wired communications using cables.

The console 22 is connected to a radiology information system (RIS) 26, which generally manages radiographic images and other information that are handled in a hospital radiological department. The RIS 26 is connected to a hospital information system (HIS) 28, which generally manages medical information in the hospital.

Figure 2:
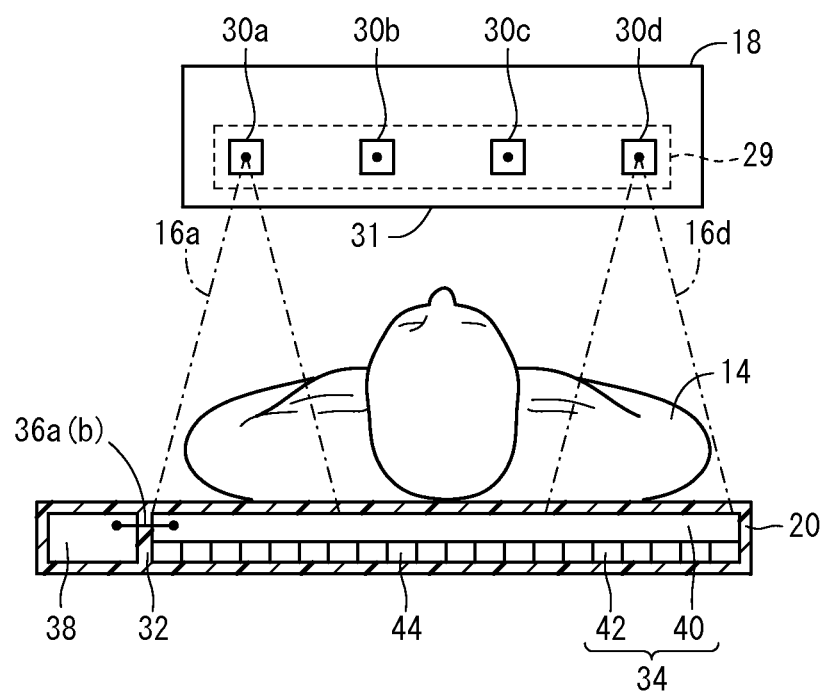
FIG. 2 is a view of a radiation output device and an electronic cassette shown in FIG. 1.
Figures 3A, 3B:
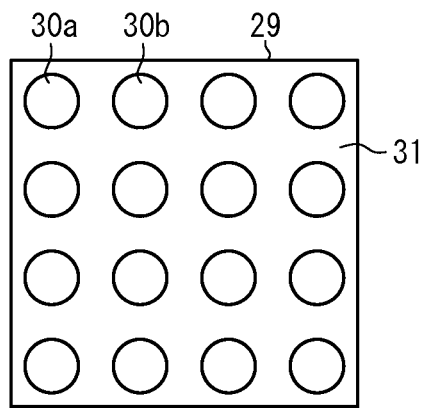
FIGS. 3A and 3B are schematic plan views showing by way of example a layout of radiation sources of the radiation output device shown in FIG. 2.

As shown in FIGS. 2 and 3A, the radiation output device 18 is a multiple-radiation-source radiation output device equipped with a radiation output portion 29 comprising a plurality of radiation sources 30a through 30p. The respective radiation sources are denoted by 30a to 30p in alphabetical order. Reference numerals with suffixes appended thereto in alphabetical order also are applied similarly to other elements, to be described below. FIG. 2 shows by way of example four radiation sources 30a through 30d as viewed on a side of the radiation output device 18, which lies perpendicular to the direction along which respective emissions of radiation 16a through 16p are output from the radiation output device 18. In a case where the radiation sources or the radiation emissions are referred to collectively rather than individually, the radiation sources or the radiation emissions may be denoted by the numerals "30" or "16" without alphabetical suffixes ("a" or the like) appended thereto.

Each of the radiation sources 30 comprises a field-electron-emission radiation source or a thermionic-emission radiation source. More specifically, each of the radiation sources 30 has a non-illustrated electron beam generating portion that applies an electron beam to a target. The target emits radiation 16 toward the subject 14 from an area (focused area) that is bombarded by the electron beam.

FIG. 3A is a schematic plan view showing by way of example a layout of radiation sources 30 of the radiation output device 18 shown in FIG. 2. In FIG. 3A, the radiation sources 30a through 30p are arranged in a matrix of four rows and four columns along a predetermined output surface 31 (planar surface in FIG. 3A). For illustrative purposes, as shown in FIG. 3B, positions of the radiation sources 30 are shown schematically as square cells in some of the figures, such as FIG. 7A. In FIG. 3B, the square cells are denoted by respective alphabetical letters corresponding to the suffixes added to the radiation sources 30 or the emissions of radiation 16.

As shown in FIG. 2, the electronic cassette 20 serves as a low-profile, portable radiographic image capturing apparatus, which is placed between the image capturing table 12 and the subject 14. The electronic cassette 20 includes a thin-walled housing 32 made of a resin or metal material permeable to radiation 16, a radiation conversion panel 34 disposed in the housing 32 for converting radiation 16 that has passed through the housing 32 into a radiographic image, and a cassette control portion 38 disposed in the housing 32 for controlling the radiation conversion panel 34 through a flexible printed circuit board (FPC) 36a, and for reading electric signals depending on the radiographic image from the radiation conversion panel 34 through another FPC 36b.

The radiation conversion panel 34 is an indirect-conversion radiation detector comprising a scintillator 42 for converting radiation 16 into electromagnetic waves having another wavelength, such as visible light, and a photoelectric transducer layer 40 for converting the electromagnetic waves into electric signals with a plurality of solid-state detecting elements (hereinafter referred to as "pixels") made of a material such as amorphous silicon (a-Si) or the like.

In FIG. 2, the radiation conversion panel 34 is of a face side reading type, i.e., an ISS (Irradiation Side Sampling) type, in which the photoelectric transducer layer 40 and the scintillator 42, which includes columnar crystals 44 of cesium iodide (CsI), are successively disposed along the irradiating direction (output direction, incident direction) in which the radiation 16 is applied. The columnar crystals 44 are formed along the irradiating direction. With such an ISS type of radiation conversion panel 34, since radiation 16 passes through the photoelectric transducer layer 40 to the scintillator 42, absorption of radiation 16 by the photoelectric transducer layer 40 should be minimized.

The photoelectric transducer layer 40 is constructed from a non-illustrated insulative substrate, plural TFTs (Thin-Film Transistors), and a photoelectric transducer, which are stacked successively along the irradiating direction. The photoelectric transducer, which is positioned near the scintillator 42, absorbs electromagnetic waves, e.g., visible light, which is emitted from the scintillator 42, and generates electric charges depending on the absorbed visible light. More specifically, the photoelectric transducer preferably includes a photoelectric transducer film made of a-Si or an organic photoconductor (OPC) material, or the like, for example, which absorbs visible light and generates electric charges responsive to the visible light. The TFTs, which read the electric charges generated by the photoelectric transducer, preferably include an active layer of a-Si, an amorphous oxide, an organic semiconductor material, carbon nanotubes, or the like. The insulative substrate, which is disposed proximate the subject 14, preferably is constituted by a flexible substrate of plastic, a substrate of aramid, or a substrate of bionanofibers. The photoelectric transducer layer 40, which includes such materials, can be fabricated according to a low-temperature process, is flexible, and minimizes absorption of radiation 16.

The scintillator 42 is fabricated by forming the columnar crystals 44 of CsI along the irradiation direction on a non-illustrated evaporated substrate, which is disposed on the surface of the photoelectric transducer layer 40 and faces toward the bottom surface of the housing 32. In a case where the scintillator 42 is made of columnar crystals 44 of thallium-added cesium iodide (CsI:Tl), and the photoelectric transducer film is made of a quinacridone based optical photoconductor (OPC), then a difference between the peak wavelength of light emitted by the scintillator 42 and the peak wavelength of light absorbed by the photoelectric transducer film can be reduced to 5 nm or smaller, thereby maximizing the amount of electric charge generated by the photoelectric transducer film. The evaporated substrate may comprise a thin aluminum (Al) substrate, which is both inexpensive and highly resistant to heat.

The material of the scintillator 42 is not limited to CsI or CsI:Tl, but may be CsI:Na (sodium-activated cesium iodide), GOS (gadolinium oxide sulfur, $Gd_2O_2S$:Tb), or the like. According to the present embodiment, the radiation conversion panel 34 may be of a reverse side reading type, i.e., a PSS (Penetration Side Sampling) type, in which the scintillator 42 and the photoelectric transducer layer 40 are disposed successively along the irradiating direction of the radiation 16. Alternatively, the radiation conversion panel 34 may be of the direct conversion type, which directly converts radiation 16 into electric signals with a plurality of pixels made of amorphous selenium (a-Se) or the like.

Figure 4:
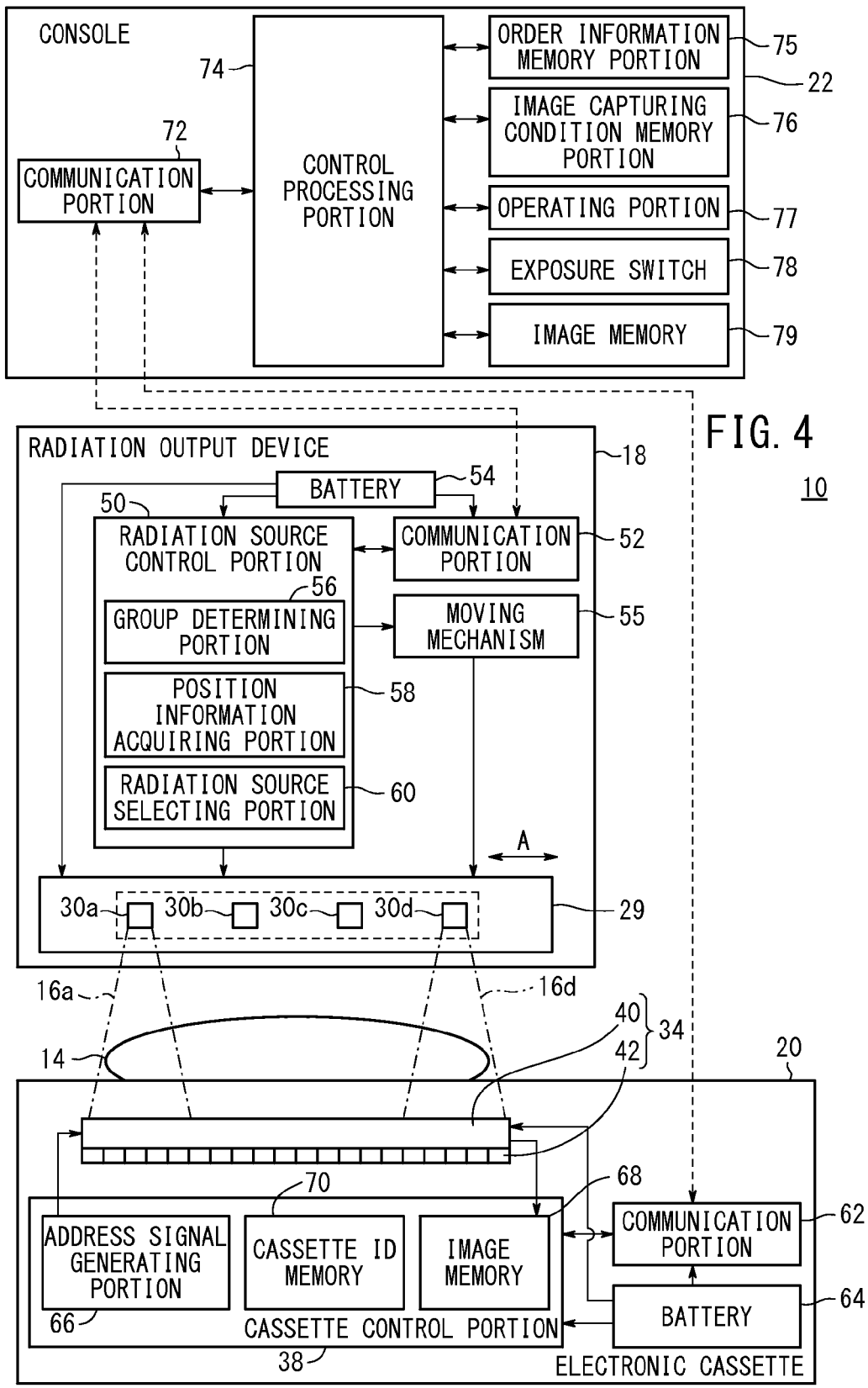
FIG. 4 is an electric block diagram of the radiographic image capturing system shown in FIG. 1.

FIG. 4 is a block diagram of the radiation output device 18, the electronic cassette 20, and the console 22, which collectively make up the radiographic image capturing system 10.

In addition to the radiation output portion 29, the radiation output device 18 includes a radiation source control portion 50 (output control portion) for controlling output of the respective emissions of radiation 16 from the radiation sources 30, a communication portion 52 for sending signals to and receiving signals from the console 22, a battery 54 for supplying electric power to the radiation output portion 29, the radiation source control portion 50, the communication portion 52, and a moving mechanism 55 for moving the radiation sources 30 in unison along the directions indicated by the arrows A.

The radiation source control portion 50 controls, i.e., turns on and off, each of the radiation sources 30 in addition to controlling the radiation dose of the respective emissions of radiation 16. In addition, the radiation source control portion 50 functions as a group determining portion 56 for determining from among the radiation sources 30 either one or both of a first radiation source group 112 (see FIG. 7A) which is used during a still image mode and a second radiation source group 114 (see also FIG. 7A) which is used during a moving image mode, a position information acquiring portion 58 for acquiring position information concerning a region of interest 110 (see FIG. 7B) of the subject 14 and the radiation output portion 29, and a radiation source selecting portion 60 for selecting at least one of the radiation sources 30 used for capturing an image. The radiation source control portion 50 supplies the moving mechanism 55 with a signal representing the distance that the radiation output portion 29 moves along the directions indicated by the arrows A.

The electronic cassette 20 includes, in addition to the radiation conversion panel 34 and the cassette control portion 38, a communication portion 62 for sending signals to and receiving signals from the console 22, and a battery 64 for supplying electric power to the photoelectric transducer layer 40, the cassette control portion 38, and the communication portion 62. The cassette control portion 38 has an address signal processing portion 66 for supplying address signals for enabling reading out of a radiographic image to the photoelectric transducer layer 40 through the FPC 36a (see FIG. 2), an image memory 68 for storing the radiographic image read from the photoelectric transducer layer 40 through the FPC 36b, and a cassette ID memory 70 for storing cassette ID information, which specifies the electronic cassette 20.

The console 22 has a communication portion 72 for sending signals to and receiving signals from the communication portions 52, 62, a control processing portion 74 for performing a predetermined control processing sequence, an order information memory portion 75 for storing order information concerning a request for capturing radiographic images of the subject 14, an image capturing condition memory portion 76 for storing image capturing conditions under which the subject 14 with is irradiated with radiation 16, an operating portion 77 such as a keyboard, a mouse, etc., an exposure switch 78 operated by a doctor or a radiological technician (hereinafter referred to as an "operator") to indicate a start timing to start emission of radiation 16 from the radiation sources 30, and an image memory 79 for storing a radiographic image, which is received from the communication portion 62 by the communication portion 72, and a radiographic image that is processed by the control processing portion 74.

The order information is generated by a doctor in charge of the RIS 26 or the HIS 28 (see FIG. 1). The order information includes subject information for identifying the subject 14, such as the name, age, gender, etc., of the subject 14, information concerning the radiation output device 18 and the electronic cassette 20 used for capturing radiographic images, and information concerning an area to be imaged of the subject 14. The image capturing conditions refer to various conditions required to apply radiation 16 to the area to be imaged of the subject 14, such as tube voltages and tube currents of the respective radiation sources 30, irradiation times of the respective radiation sources 30, etc., for example.

Figure 5:
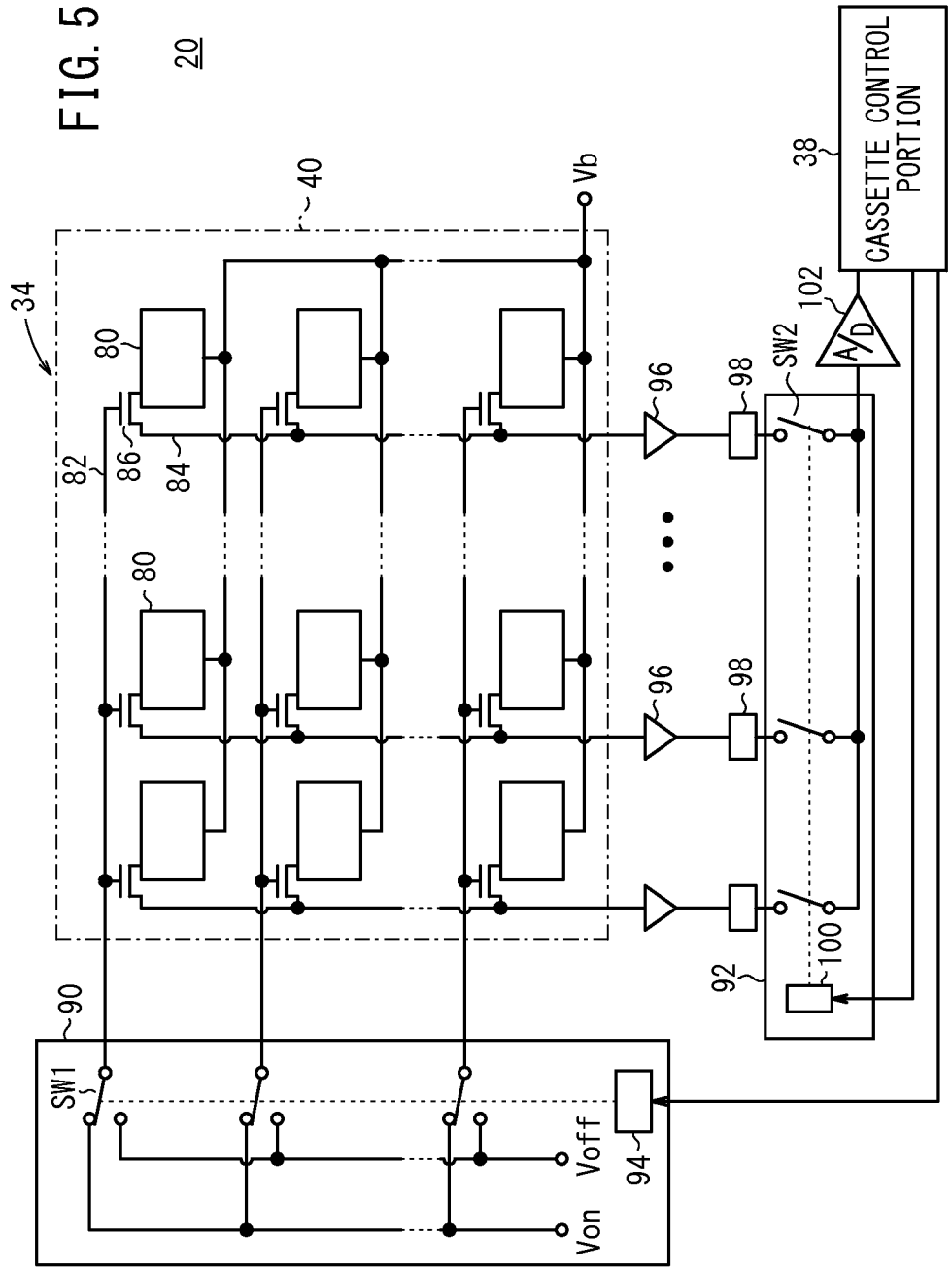
FIG. 5 is a circuit diagram of a circuit arrangement of the electronic cassette shown in FIG. 4.

FIG. 5 is a circuit diagram of a circuit arrangement of the electronic cassette 20.

The photoelectric transducer layer 40 referred to above comprises an array of TFTs 86 arranged in rows and columns, and a plurality of pixels 80 made of a material such as a-Si or the like for converting electromagnetic waves (visible light), which have been converted from the radiation 16 by the scintillator 42, into electric signals. The pixels 80 are disposed on the array of TFTs 86. The pixels 80, which are supplied with a bias voltage Vb from the battery 64 (see FIG. 4), store electric charges that are generated in a case where the pixels 80 convert electromagnetic waves into electric signals (analog signals). The TFTs 86 are turned on successively along each row at a time, whereupon the stored electric charges are read from the pixels 80 as an image signal.

The TFTs 86 are connected to the respective pixels 80. Gate lines 82, which extend parallel to the rows, and signal lines 84, which extend parallel to the columns, are connected to the TFTs 86. The gate lines 82 are connected to a line scanning driver 90, and the signal lines 84 are connected to a multiplexer 92. The gate lines 82 are supplied with control signals Von, Voff from the line scanning driver 90 for turning on and off the TFTs 86 along the rows. The line scanning driver 90 includes a plurality of switches SW1 for switching between the gate lines 82, and an address decoder 94 for supplying a selection signal for selecting one of the switches SW1 at a time. The address decoder 94 is supplied with an address signal from the address signal processing portion 66 (see FIG. 4) of the cassette control portion 38.

The signal lines 84 are supplied with electric charges through the TFTs 86, which are arranged in columns, and the electric charges are stored in the pixels 80. The electric charges supplied to the signal lines 84 are amplified by amplifiers 96. The amplifiers 96 are connected through respective sample and hold circuits 98 to the multiplexer 92. The multiplexer 92 includes a plurality of switches SW2 for successively switching between the signal lines 84, and an address decoder 100 for outputting selection signals for selecting one of the switches SW2 at a time. The address decoder 100 is supplied with address signals from the address signal processing portion 66. The multiplexer 92 has an output terminal connected to an A/D converter 102. The A/D converter 102 converts radiographic image information into digital image signals, which are supplied to the cassette control portion 38.

The TFTs 86, which function as switching devices, may be combined with another image capturing device such as a CMOS (Complementary Metal-Oxide Semiconductor) image sensor or the like. Alternatively, the TFTs 86 may be replaced with a CCD (Charge-Coupled Device) image sensor for shifting and transferring electric charges with shift pulses that correspond to gate signals in the TFTs 86.

In the present description, an image capturing mode for acquiring a radiographic image in a single image capturing event is referred to as a "still image mode", whereas an image capturing mode for capturing a succession of radiographic images (including tomosynthesis images) in successive image capturing events is referred to as a "moving image mode (fluoroscopic image mode)". In the moving image mode, radiation 16 is emitted, whereby radiographic images are acquired repeatedly in succession at relatively short time intervals (at a predetermined frame rate). In the moving image mode, various known moving image capturing techniques, such as a progressive scanning technique, an interlaced scanning technique, a binning technique, etc., may be applied.

[Operations of Radiographic Image Capturing System 10]

Operations of the radiographic image capturing system 10 according to the present embodiment will be described below primarily with reference to the flowchart shown in FIG. 6 and the block diagram shown in FIG. 4.

Figure 6:
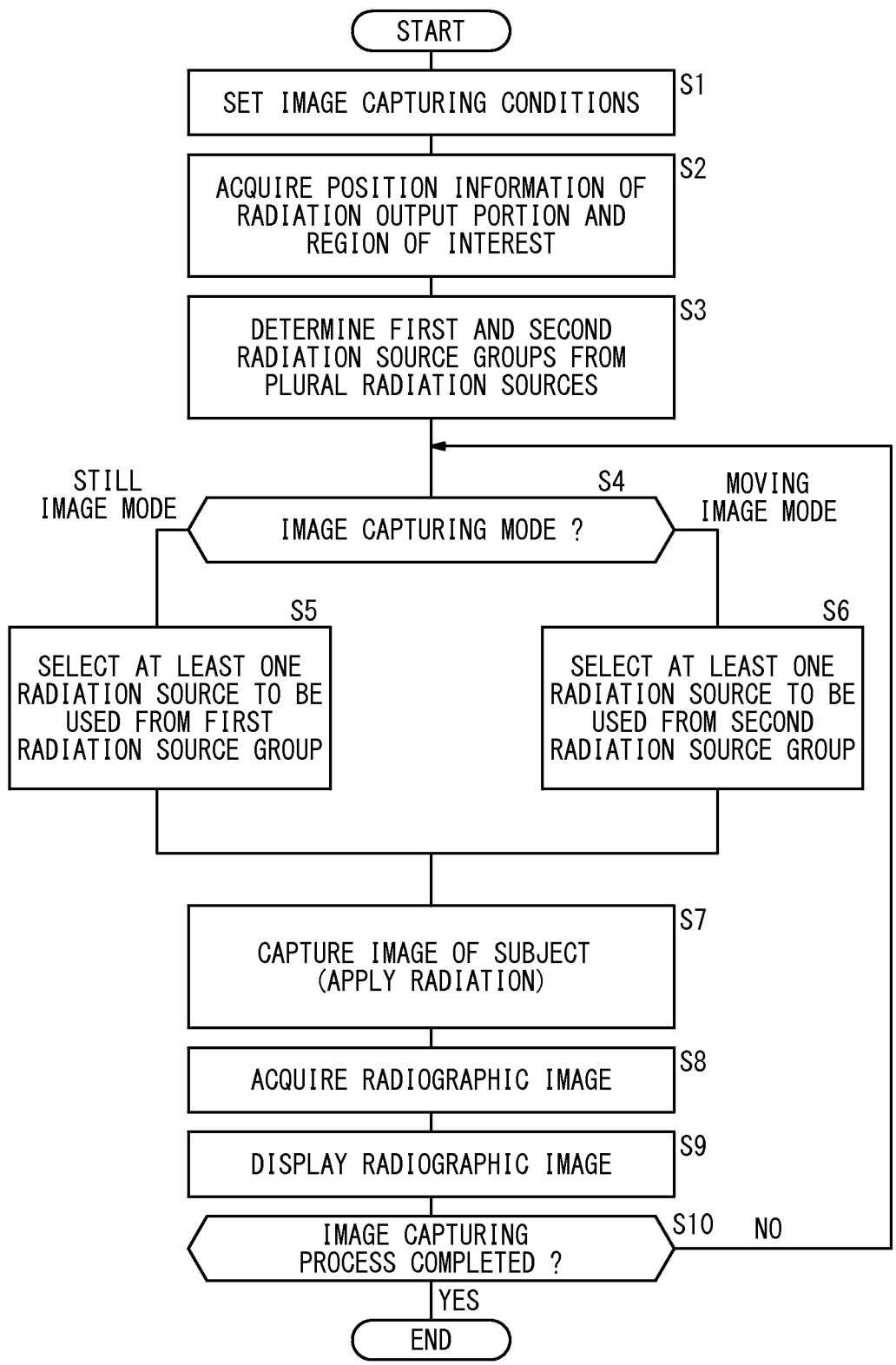
FIG. 6 is a flowchart of an operation sequence of the radiographic image capturing system shown in FIG. 1.

In step S1 of FIG. 6, the control processing portion 74 of the console 22 sets image capturing conditions (tube voltage, tube current, irradiation time) for applying radiation 16 from the respective radiation sources 30 to an area to be imaged of the subject 14, based on the order information. Such order information refers to information acquired from the RIS 26 (or the HIS 28), which is temporarily stored in the order information memory portion 75.

Thereafter, the control processing portion 74 stores the set image capturing conditions in the image capturing condition memory portion 76, and sends the set image capturing conditions through the communication portion 72 and the communication portion 52 to the radiation output device 18. The control processing portion 74 also sends the set image capturing conditions or the order information through the communication portion 72 and the communication portion 62 to the electronic cassette 20 via a wireless link. Thereafter, the cassette control portion 38 stores the image capturing conditions, etc., which are received through the communication portion 62, in at least one of the image memory 68 and the cassette ID memory 70. The image capturing conditions or the order information may be sent either immediately after the image capturing conditions have been set, or in response to a request to send the image capturing conditions and the order information from the radiation output device 18 or the electronic cassette 20.

Figure 7A:
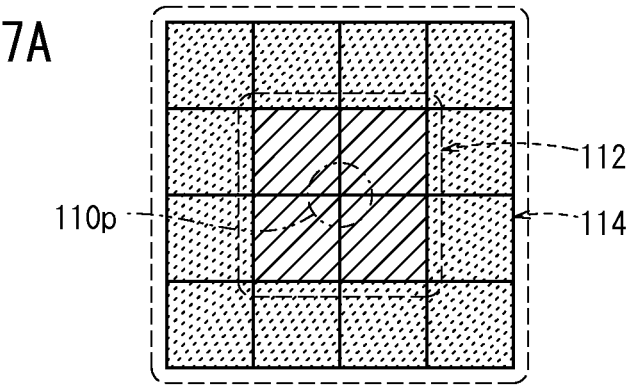
FIG. 7A is a diagram showing by way of example first and second radiation source groups determined for capturing an image of a region of interest located in a first position.
Figure 7B:
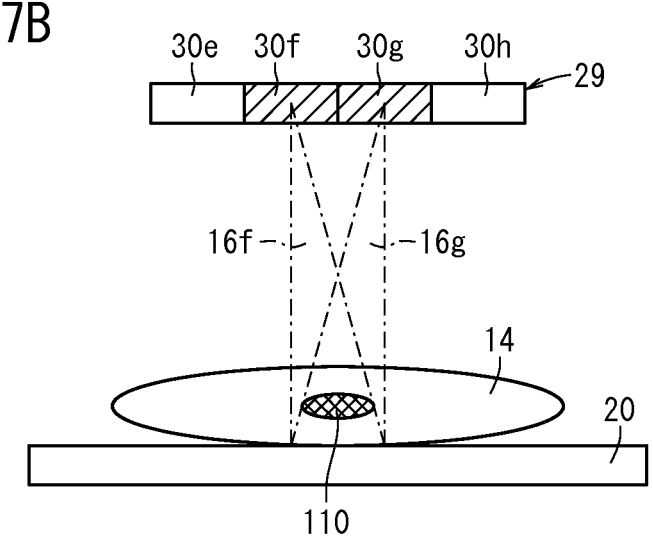
FIG. 7B is a diagram showing a manner in which radiation is emitted toward the region of interest located in the first position, in the case that the radiographic image capturing system is in a still image mode.

In step S2, the position information acquiring portion 58 of the radiation output device 18 acquires position information concerning the radiation output portion 29 and the region of interest 110 (see FIG. 7B). The radiation output portion 29 may be in a predetermined reference position, e.g., a central position on the output surface 31, or an absolute position in reference to each of the radiation sources 30a through 30p. The region of interest 110 may be in an absolute position, which is measured by some means, or a position that is estimated from the order information, which represents the position and posture of the subject 14 and the area to be imaged of the subject 14.

In step S3, the group determining portion 56 of the radiation output device 18 determines, from among the radiation sources 30, at least one of a first radiation source group 112 which is used in the still image mode and a second radiation source group 114 which is used in the moving image mode.

As shown in FIG. 7A, the radiation sources 30 that belong to the first radiation source group 112 are cells shown in hatching, i.e., the four radiation sources 30f, 30g, 30j, and 30k, which are centrally located on the radiation output portion 29. The radiation sources 30 that belong to the second radiation source group 114 are cells shown as stippled, i.e., the remaining twelve radiation sources 30a through 30d, 30e, 30h, 30i, 30l, and 30m through 30p. Details of a process for determining the first radiation source group 112 and the second radiation source group 114 will be described later.

In step S4, in response to a command to start capturing a radiographic image of the subject 14, the radiation source control portion 50 of the radiation output device 18 judges whether the image capturing mode to be carried out is a still image mode or a moving image mode.

The operator inserts the electronic cassette 20 (see FIG. 1) between the subject 14 and the image capturing table 12, positions the subject 14, and then turns on the exposure switch 78. The control processing portion 74 synchronizes the start of emission of radiation 16 from the radiation output portion 29 with the detection and conversion of radiation 16 by the radiation conversion panel 34 into a radiographic image. The control processing portion 74 generates a synchronizing control signal for capturing a radiographic image of the area to be imaged of the subject 14. The control processing portion 74 sends the generated synchronizing control signal from the communication portion 72 to the communication portions 52, 62 via wireless links. In a case where the radiation source control portion 50 receives the synchronizing control signal through the communication portion 52, a radiographic image of the area to be imaged of the subject 14 starts to be captured under the image capturing conditions set in step S1. Thereafter, by referring to the order information received from the console 22, the radiation source control portion 50 determines the image capturing mode.

In a case where the radiation source control portion 50 judges that the image capturing mode is a still image mode, then control proceeds to step S5, whereupon the radiation source selecting portion 60 selects at least one radiation source 30 from among the first radiation source group 112, which is used in the still image mode. It is assumed that the radiation source selecting portion 60 selects all of the radiation sources 30 belonging to the first radiation source group 112, i.e., the four radiation sources 30f, 30g, 30j, and 30k.

In a case where the radiation source control portion 50 judges that the image capturing mode is a moving image mode, then control proceeds to step S6, whereupon the radiation source selecting portion 60 selects at least one radiation source 30 from among the second radiation source group 114, which is used in the moving image mode. It is assumed that the radiation source selecting portion 60 selects all of the radiation sources 30 belonging to the second radiation source group 114, i.e., the twelve radiation sources 30a through 30d, 30e, 30h, 30i, and 30l through 30p.

In step S7, the radiographic image capturing system 10 captures a radiographic image of the subject 14 by emitting radiation 16 from the radiation sources 30 that were selected in step S5 or step S6. More specifically, the radiation source control portion 50 controls the radiation sources 30 to apply radiation 16 at a predetermined dose from the radiation sources 30 to the area to be imaged of the subject 14 for a predetermined irradiation time according to the image capturing conditions acquired from the console 22.

Preferred image capturing processes carried out during the image capturing modes will be described in detail below with reference to FIGS. 7A through 10B. For the sake of brevity, only certain ones of the radiation sources 30, i.e., the radiation sources 30 belonging to the second row of the matrix shown in FIG. 3B, will be described by way of illustrative example.

Figure 7C:
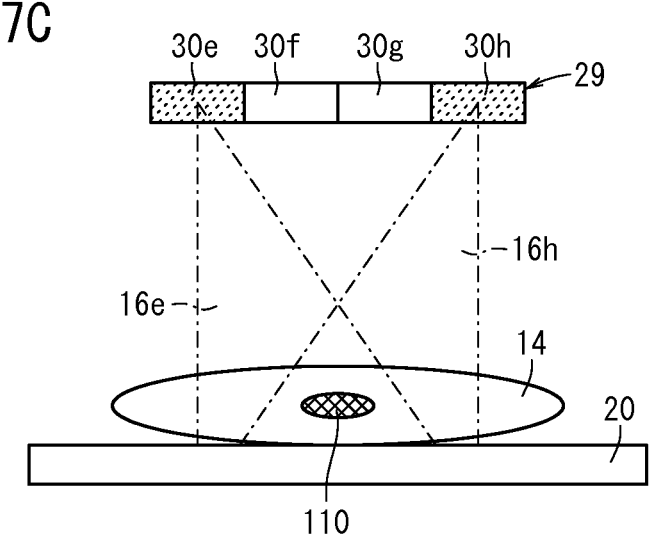
FIG. 7C is a diagram showing a manner in which radiation is emitted toward the region of interest located in the first position, in the case that the radiographic image capturing system is in a moving image mode.

According to a first example, it is assumed that, in a case where the region of interest 110 is projected onto the output surface 31 along a direction normal to the electronic cassette 20, a projected image 110p (indicated by the two-dot-and-dash line in FIG. 7A) of the region of interest 110 lies on four cells (f, g, j, k), as shown in FIG. 3B. An actual position of the region of interest 110 shown in FIGS. 7B and 7C is referred to as a first position. Stated otherwise, the radiation sources 30f, 30g, 30j, 30k are present directly above the first position along a direction normal to the principal surface of the electronic cassette 20.

As shown in FIG. 7B, during an image capturing process in the still image mode, two radiation sources 30f, 30g of the four radiation sources 30e through 30h that belong to the second row emit respective emissions of radiation 16f, 16g. The emissions of radiation 16f, 16g pass through the region of interest 110 substantially from the front side thereof, and are applied substantially perpendicularly to the electronic cassette 20. Consequently, it is possible to obtain a high-quality radiographic image, which is almost free of geometrical distortions. In order to achieve higher image quality and reduce the dose of radiation to which the subject 14 is exposed, the image capturing process may be carried out with a smaller irradiation field, which is made up of the radiation sources 30f, 30g, than in the moving image mode.

As shown in FIG. 7C, during an image capturing process in the moving image mode, two radiation sources 30e, 30h of the four radiation sources 30e through 30h that belong to the second row emit respective emissions of radiation 16e, 16h. The emissions of radiation 16e, 16h pass through the region of interest 110 in a slightly oblique manner, and are applied substantially perpendicularly to the electronic cassette 20. A moving image captured in this manner primarily is used in order to monitor a change in the state of the subject 14, and hence, the moving image is sufficiently useful for this purpose. In order to reduce the dose of radiation to which the subject 14 is exposed, the image capturing process may be carried out with a smaller dose per unit time of the radiation 16f, 16g than in the still image mode.

The group determining portion 56 determines the first radiation source group 112 and the second radiation source group 114, such that each of the radiation sources 30 belongs to either one of the groups. Therefore, both a still image and a moving image can simultaneously be captured of the same subject 14 and the same region of interest 110. In this case, the radiographic image capturing system 10 requires an arrangement, such as an arrangement having two radiation detectors, for separately acquiring the still image and the moving image.

According to a typical example, which involves frequent switching between the still image mode and the moving image mode, the operator may initially select the moving image mode and carry out an image capturing process in the moving image mode. Then, the operator may position the subject 14 while visually confirming the moving image of the subject 14, and thereafter, switch from the moving image mode to the still image mode in order to carry out a main image capturing mode (and repeat the whole process).

Even in a case where the position of the region of interest 110 differs from that of the first position (see FIGS. 7B and 7C) described above, suitable radiation sources 30 can be selected based on the above principles.

Figure 8A:
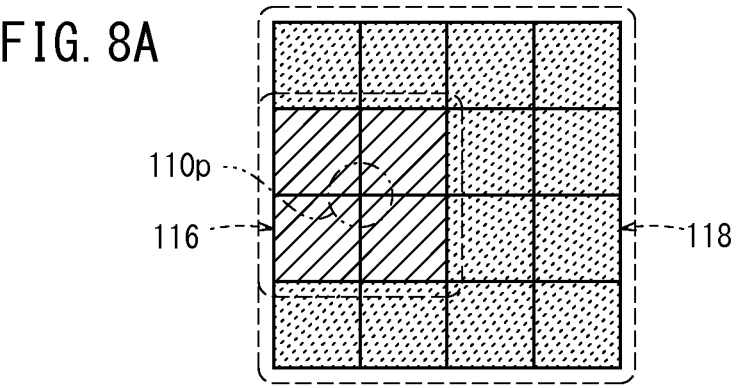
FIG. 8A is a diagram showing by way of example first and second radiation source groups determined for capturing an image of a region of interest located in a second position.
Figure 8B:
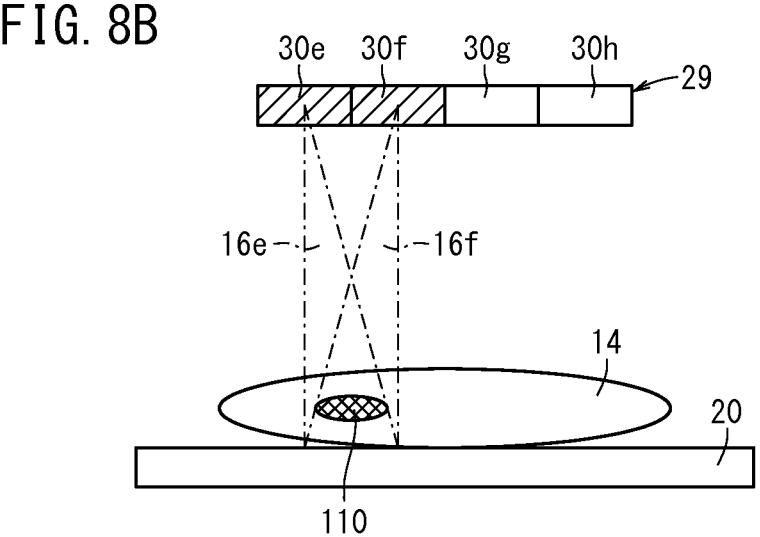
FIG. 8B is a diagram showing a manner in which radiation is emitted toward the region of interest located in the second position, in the case that the radiographic image capturing system is in a still image mode.
Figure 8C:
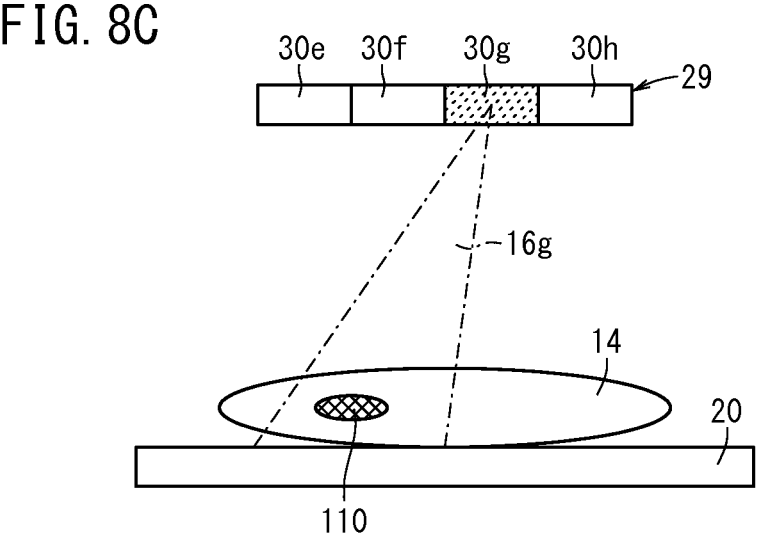
FIG. 8C is a diagram showing a manner in which radiation is emitted toward the region of interest located in the second position, in the case that the radiographic image capturing system is in a moving image mode.

According to a second example, it is assumed that, in a case where the region of interest 110 is projected onto the output surface 31 along a direction normal to the electronic cassette 20, a projected image 110p (indicated by the two-dot-and-dash line in FIG. 8A) of the region of interest 110 lies on four cells (e, f, i, j), as shown in FIG. 3B. The actual position of the region of interest 110 shown in FIGS. 8B and 8C is referred to as a second position.

The group determining portion 56 classifies radiation sources 30, the actual distances of which from the region of interest 110 (to the projected image 110p on the output surface 31) are relatively small, into a first radiation source group (see step S3). As a result, as shown in FIG. 8A, the radiation sources 30, which belong to a first radiation source group 116, are the four radiation sources 30e, 30f, 30i, and 30j that reside in a central left area of the radiation output portion 29. The radiation sources 30, which belong to a second radiation source group 118, are the remaining twelve radiation sources 30a through 30d, 30g, 30h, 30k, 30l, and 30m through 30p.

For an image capturing process in the still image mode, the radiation source selecting portion 60 selects at least one of the radiation sources 30 to be used in the image capturing process from among the first radiation source group 116 (see step S5). For example, it is assumed that the radiation source selecting portion 60 selects all four of the radiation sources 30e, 30f, 30i, 30j. Then, as shown in FIG. 8B, two radiation sources 30e, 30f from among the four radiation sources 30e through 30h that belong to the second row emit respective emissions of radiation 16e, 16f.

For an image capturing process in the moving image mode, the radiation source selecting portion 60 selects at least one of the radiation sources 30 to be used in the image capturing process from among the second radiation source group 118 (see step S6). For example, it is assumed that the radiation source selecting portion 60 selects eight radiation sources 30a through 30c, 30g, 30k, and 30m through 30o having relatively small irradiation angles with respect to the region of interest 110, from among the remaining radiation sources 30a through 30d, 30g, 30h, 30k, 30l, and 30m through 30p. Then, as shown in FIG. 8C, one radiation source 30g from among the four radiation sources 30e through 30h that belong to the second row emits radiation 16g.

Consequently, depending on the positional relationship between the region of interest 110 (second position) and each of the radiation sources 30, at least one radiation source 30 is selected as a radiation source to be used for the image capturing process, thereby making it possible to capture a radiographic image of the region of interest 110 in a manner that is suitable for the position of the region of interest 110, regardless of whether the image capturing mode is the still image mode or the moving image mode.

Figure 9A:
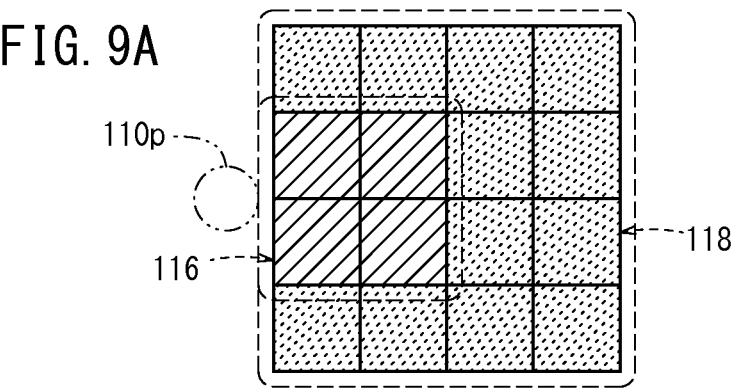
FIG. 9A is a diagram showing by way of example first and second radiation source groups determined for capturing an image of a region of interest located in a third position.
Figure 9B:
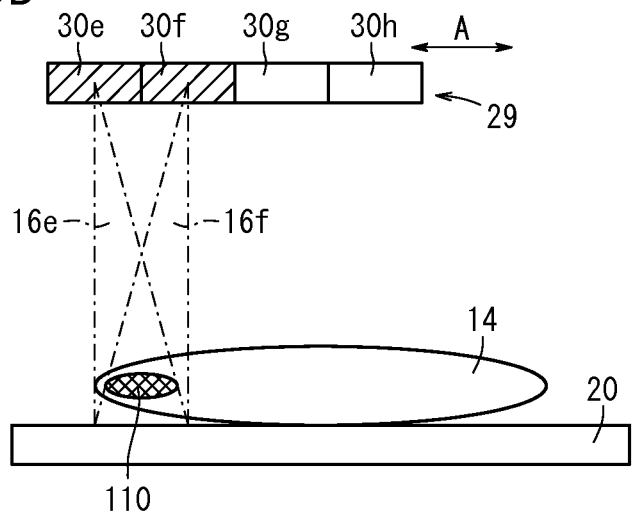
FIG. 9B is a diagram showing a manner in which radiation is emitted toward the region of interest located in the third position, in the case that the radiographic image capturing system is in a still image mode.
Figure 9C:
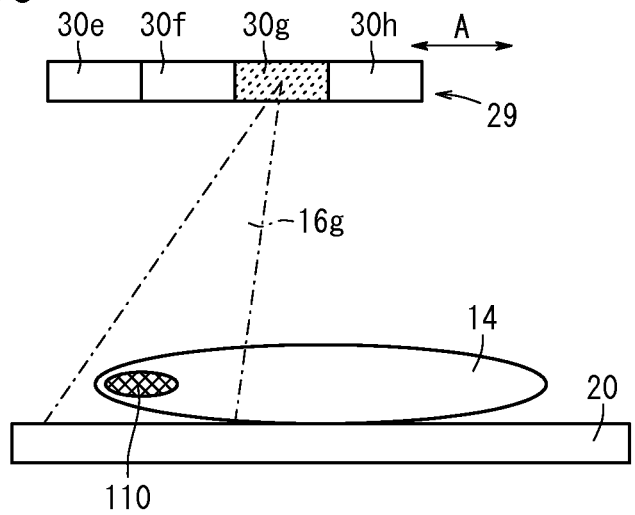
FIG. 9C is a diagram showing a manner in which radiation is emitted toward the region of interest located in the third position, in the case that the radiographic image capturing system is in a moving image mode.

According to a third example, it is assumed that, in a case where the region of interest 110 is projected onto the output surface 31 along a direction normal to the electronic cassette 20, a projected image 110p (indicated by the two-dot-and-dash line in FIG. 9A) of the region of interest 110 lies on two cells (e, i), as shown in FIG. 3B. The actual position of the region of interest 110 shown in FIGS. 9B and 9C is referred to as a third position.

The radiation source control portion 50 controls the moving mechanism 55 in order to move the radiation output portion 29 a predetermined distance to the left (commensurate with one and a half cells, for example) along the direction indicated by the arrow A. At this time, the radiation output portion 29 and the region of interest 110 have the same positional relationship as shown in FIGS. 8B and 8C. Thereafter, radiation sources 30 can be selected in the same manner as though the region of interest 110 were present in the second position.

Figure 10A:
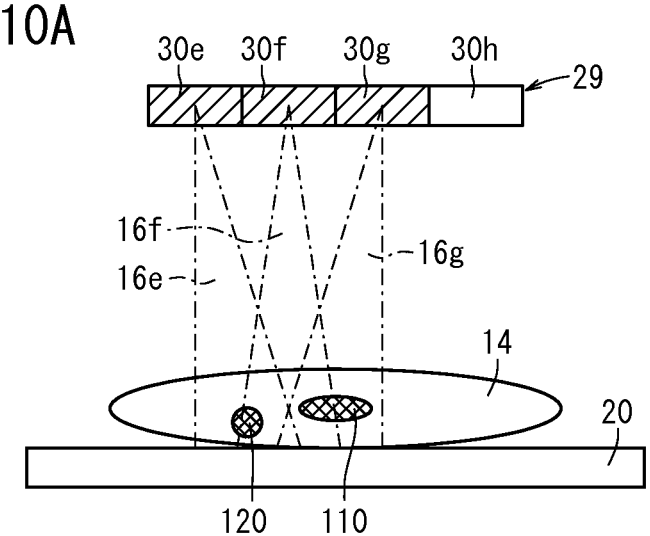
FIG. 10A is a diagram showing a manner in which radiation is emitted toward plural regions of interest, in the case that the radiographic image capturing system is in a still image mode.
Figure 10B:
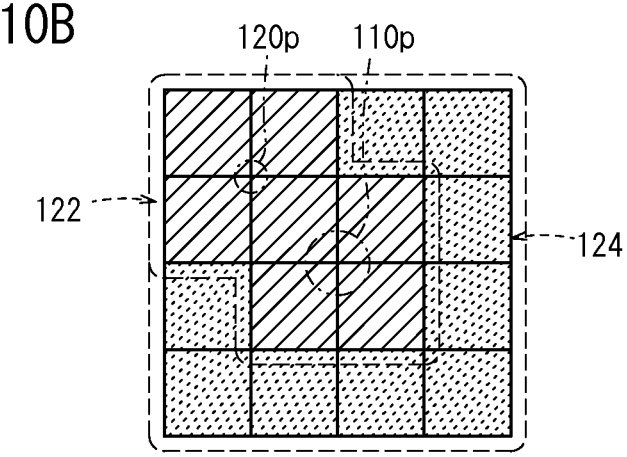
FIG. 10B is a diagram showing by way of example first and second radiation source groups determined for capturing an image of plural regions of interest.

According to a fourth example, as shown in FIG. 10A, the subject 14 has a plurality of regions of interest, or more specifically, has another region of interest 120 in addition to the region of interest 110 in the first position. It is assumed that, in a case where the region of interest 120 is projected onto the output surface 31 along a direction normal to the electronic cassette 20, a projected image 120p (indicated by the two-dot-and-dash line in FIG. 10B) of the region of interest 120 lies on four cells (a, b, e, f), as shown in FIG. 3B. The actual position of the region of interest 120 shown in FIG. 10B is referred to as a fourth position.

The group determining portion 56 classifies radiation sources 30, the actual distances of which from the region of interest 110 (first position) and the region of interest 120 (fourth position) (to the projected images 110p, 120p on the output surface 31) are relatively small, into a first radiation source group (see step S3). As a result, the radiation sources 30 that belong to a first radiation source group 122 are the seven radiation sources 30a, 30b, 30e through 30g, 30j, and 30k, which reside in an upper left area of the radiation output portion 29. The radiation sources 30 that belong to a second radiation source group 124 are the remaining nine radiation sources 30c, 30d, 30h, 30i, and 30l through 30p.

Then, as shown in FIG. 10A, three radiation sources 30e through 30g from among the four radiation sources 30e through 30h that belong to the second row emit respective emissions of radiation 16e through 16g.

In common with the first through fourth examples, in the event that the radiation source control portion 50 selects two or more radiation sources 30, the radiation source control portion 50 may select a cluster of radiation sources 30, as the output surface 31 is viewed in plan. In such a cluster of radiation sources 30, each of the radiation sources 30 is positioned adjacent to at least one other radiation source 30. In this manner, the respective emissions of radiation 16, which are emitted simultaneously from the selected radiation sources 30 to the subject 14, are closely bundled, so as to prevent the resultant radiographic image from suffering from geometric distortions.

For an image capturing process in the moving image mode, the radiation source control portion 50 may switch between the radiation sources 30, such that selected radiation sources 30 are used at predetermined time intervals. For example, in the second radiation source group 114 shown in FIG. 7A, the radiation source control portion 50 successively selects the radiation sources 30*a*, 30*c*, 30*e*, 30*h*, 30*i*, . . . , one at a time, within respective frames. The radiation source control portion 50 thus selects the radiation source 30*c*, which is in a non-adjacent position to the radiation source 30*a* used immediately before and uses the radiation sources 30 substantially at the same frequency as each other, for thereby dissipating heat efficiently from the target of the radiation sources 30, and effectively preventing the radiation output device 18 from becoming overheated.

As descried above, the radiographic image capturing system 10 emits radiation 16 from radiation sources 30 selected depending on the image capturing mode, thereby capturing a radiographic image of the subject 14 (step S7). The radiation output device 18 may automatically change the radiation sources 30 that are used for capturing the radiographic image depending on instructions to change image capturing conditions such as the image capturing mode, the region of interest, etc. Alternatively, the radiation output device 18 may automatically change the radiation sources 30 that are used for capturing a radiographic image depending on a manual action made by the operator.

In step S8, the radiographic image capturing system 10 acquires a radiographic image of the subject 14. Operations of various components of the radiographic image capturing system 10 will be described in detail below.

Radiation 16 that has passed through the subject 14 (imaged region) reaches the radiation conversion panel 34 of the electronic cassette 20. The scintillator 42 having the columnar crystals 44 of CsI or CsI:Tl emits visible light at an intensity depending on the intensity of the radiation 16, and the pixels 80 of the photoelectric transducer layer 40 convert the visible light into electric signals and store the signals as electric charges.

In step S4, the control processing portion 74 sends the synchronizing control signal through the communication portion 72 to the communication portion 62. After the cassette control portion 38 has received the synchronizing control signal from the communication portion 62, the address signal processing portion 66 supplies address signals to the line scanning driver 90 and the multiplexer 92, so as to initiate reading of the electric charge information representing a radiographic image of the subject 14 from the pixels 80.

More specifically, the address decoder 94 of the line scanning driver 90 supplies a selection signal for selecting one of the switches SW1 according to the address signals sent from the address signal processing portion 66, and supplies control signals Von to the gates of the TFTs 86 connected to the corresponding gate lines 82. The address decoder 100 of the multiplexer 92 supplies selection signals according to the address signals sent from the address signal processing portion 66, thereby successively selecting the switches SW2. Through the signal lines 84, the address decoder 100 successively reads a radiographic image represented by the electric charge information held by the pixels 80 connected to the gate lines 82, which are selected by the line scanning driver 90.

The radiographic image read from the pixels 80 connected to the selected gate lines 82 is amplified by the amplifiers 96, sampled by the sample and hold circuits 98, and supplied through the multiplexer 92 to the A/D converter 102, which converts the radiographic image into digital signals. The digital signals, which represent the radiographic image, are temporarily stored in the image memory 68 of the cassette control portion 38.

Similarly, the address decoder 94 of the line scanning driver 90 successively selects switches SW1 according to the address signals sent from the address signal processing portion 66. Through the signal lines 84, the address decoder 94 reads a radiographic image represented by the electric charge information held by the pixels 80 connected to the gate lines 82, and stores the radiographic image in the image memory 68 of the cassette control portion 38 through the multiplexer 92 and the A/D converter 102.

In a case where the image capturing mode is the moving image mode, the cassette control portion 38 acquires a radiographic image from the electric charges stored by the pixels 80 at a preset frame rate, e.g., a frame rate of 15 to 60 frames/second. In a case where the electric charges are read by an interlaced scanning technique, for example, the frame rate can be increased, and the burden on the signal processing system can be reduced.

In step S9, the display device 24 receives the radiographic image, which is acquired from the electronic cassette 20 via the console 22, and displays the received radiographic image as an image to be interpreted by the operator.

More specifically, in response to a transmission request from the console 22, which is received through the communication portion 62, the cassette control portion 38 sends the radiographic image stored in the image memory 68 and the cassette ID information stored in the cassette ID memory 70 through the communication portion 62 to the console 22 via a wireless link. Thereafter, the control processing portion 74 performs a predetermined image processing technique, e.g., a known type of image reconstructing process, on the received radiographic image in order to generate an image that can be interpreted by the operator. The control processing portion 74 sends the generated image through the communication portion 72 to the display device 24 via a wireless link.

In step S10, the operator observes the image displayed on the display device 24 in order to judge whether or not a desired radiographic image has been obtained. In a case where the operator determines that a desired radiographic image has been obtained (YES), then the image capturing process on the subject 14 is brought to an end. In a case where the operator judges that a desired radiographic image has not been obtained (NO), then control returns to step S4, and an image capturing process is carried out again on the subject 14.

As described above, inasmuch as at least one radiation source 30 for emitting radiation 16 is selected from among the plural radiation sources 30 depending on whether the image capturing mode is the still image mode or the moving image mode, it is possible to emit radiation 16 from positions suitable for the image capturing mode, without the need for moving the radiation sources 30 or positioning the subject 14 differently. Consequently, the efficiency with which the operator works in capturing images in the still image mode and the moving image mode is significantly increased.

[Applications of the Radiographic Image Capturing Process]

Applications of the radiographic image capturing process in the still image mode and the moving image mode will be described below. An example is presented in which a contrast agent for highlighting a portion of a radiographic image is used for capturing an image of a particular region (e.g., the heart, a blood vessel, or the like) having a minute structure.

First, the operator injects a contrast agent into the subject 14 through a blood vessel (artery or vein) of the subject 14. Immediately after injecting the contrast agent, the operator captures a radiographic image of the subject 14 in the moving image mode, and checks the timing for the contrast agent to reach the particular region while viewing the moving image of the particular region. During the moving image mode, radiographic image capturing processes are performed sequentially at a wide angle (see FIGS. 8C and 7C) and with low resolution. Upon flowing through the blood vessels, the injected contrast agent circulates through the body of the subject 14, and after elapse of a predetermined time, the contrast agent reaches the particular region such as the heart or the like.

In a case where it is judged that the contrast agent has reached the particular region, then the radiation source control portion 50 switches from the moving image mode to a continuous still image capturing mode, in response to an action made on the operating portion 77 by the operator. The continuous still image capturing mode refers to an image capturing mode for capturing successive images in a still image mode at longer time intervals than the frame interval of the moving image mode. In the continuous still image capturing mode, capturing of radiographic images is performed at a narrow angle (see FIGS. 7B and 8B) and with high resolution. In other words, images of the particular region are captured in the still image mode during a time zone in which a large amount of the contrast agent has reached the particular region, thereby providing diagnostic images that are high in contrast and resolution. Since the still images are successively captured in the continuous still image capturing mode, no loss in timing occurs, even though the images are captured using the contrast agent. Furthermore, the obtained still images are successively connected to allow the operator to easily grasp the particular region during movement thereof.

Since the radiation source control portion 50 successively controls the emissions of radiation 16 depending on the still image mode and at a longer time interval than the frame interval of the moving image mode, images can reliably be captured in the still image mode without any loss in timing, even though the states of the target to be imaged (characteristics of the radiographic images) change from time to time.

[Modifications of the Present Embodiment]

Modifications (first and second modifications) of the present embodiment will be described below with reference to FIGS. 11 and 12. Parts of the modifications, which are identical to those of the present embodiment, are denoted by identical reference characters, and such features will not be described in detail below.

(First Modification)

A radiation output portion 130 according to a first modification differs from the present embodiment (see FIG. 3A) in relation to the layout (number and positions) of the radiation sources 30.

Figure 11:
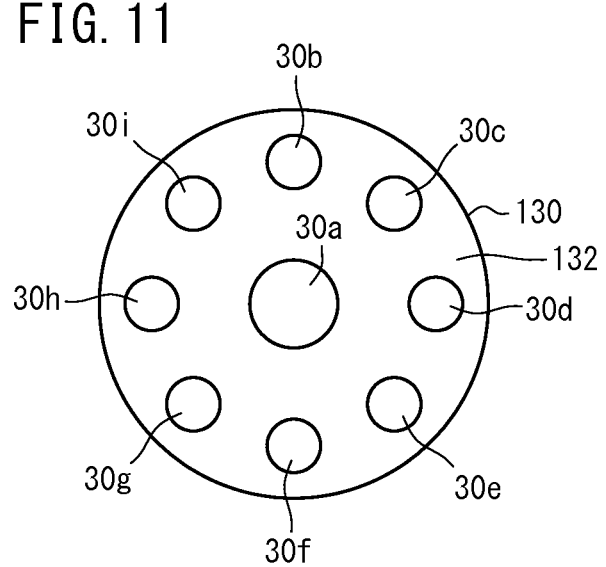
FIG. 11 is a schematic plan view showing by way of example a layout of radiation sources of a radiation output device according to a first modification.

As shown in FIG. 11, the radiation output portion 130 has a circular output surface 132 for emitting radiation 16. The radiation output portion 130 includes a radiation source 30a disposed at a central position of the output surface 132, and eight radiation sources 30b through 30i disposed respectively at equal intervals along the circumferential edge of the output surface 132. The size of the radiation source 30a is greater than the size of the radiation sources 30b through 30i. The group determining portion 56 classifies the radiation source 30a into the first radiation source group, which may be used solely in the still image mode, whereas the other radiation sources 30b through 30i may be selected depending on at least one of the image capturing mode (still image mode, moving image mode) and the positional relationship with respect to the region of interest 110.

According to the present embodiment, the output surfaces 31, 132 are planar in shape. However, the output surfaces 31, 132 may be of a curved shape or another shape. In addition, the number or positions of the radiation sources 30 may be changed appropriately as required.

(Second Modification)

A radiographic image capturing system 140 according to a second modification differs from the present embodiment (see FIG. 4) as to the arrangement of the output control portion for controlling how the radiation 16 is output.

As shown in FIG. 12, the radiation output device 18 includes a radiation source control portion 142 having functions to turn on and off the radiation sources 30, so as to control the dose of radiation 16. The console 22 includes a radiation source determining portion 144 having the functions of a group determining portion 56, a position information acquiring portion 58, and a radiation source selecting portion 60, in addition to a communication portion 72, a control processing portion 74, an order information memory portion 75, an image capturing condition memory portion 76, an operating portion 77, an exposure switch 78, and an image memory 79.

Similar to the present embodiment, the radiation source determining portion 144 selects at least one radiation source 30, which is used in a main image capturing process, from among the radiation sources 30a through 30p. The control processing portion 74 sends information (hereinafter referred to as "radiation source selection information") concerning the selection result made by the radiation source determining portion 144 to the radiation source control portion 142 through the communication portion 72 and the communication portion 52. Based on the received radiation source selection information, the radiation source control portion 142 controls the radiation sources 30 to emit radiation 16.

More specifically, the output control portion according to the second modification comprises the radiation source control portion 142 of the radiation output device 18 and the radiation source determining portion 144 of the console 22. The output control portion, which is constructed in the foregoing manner from a plurality of devices (the radiation output device 18 and the console 22), offers the same advantages as those of the present embodiment.

The present invention is not limited to the embodiment described above. It is a matter of course that various changes can freely be made to the embodiment without departing from the scope of the present invention.

The invention claimed is:

1. A radiographic image capturing system comprising:
   a radiation output device having a plurality of radiation sources arranged along a predetermined surface; and
   an output control portion for controlling emissions of radiation, respectively, from the radiation sources of the radiation output device,
   wherein the output control portion includes a radiation source selecting portion for selecting at least one of the radiation sources for emitting the radiation depending on whether an image capturing mode is a still image mode for capturing a radiographic image in a single image capturing event, or a moving image mode for capturing a succession of radiographic images in successive image capturing events.

2. The radiographic image capturing system according to claim 1, wherein the predetermined surface comprises a planar surface; and
   the radiation sources are arranged in a matrix.

3. The radiographic image capturing system according to claim 1, wherein the output control portion further includes a group determining portion for determining a first radiation source group to be used in the still image mode from among the radiation sources; and the radiation source selecting portion selects at least one of the radiation sources from among the first radiation source group determined by the group determining portion in a case where the image capturing mode is the still image mode.

4. The radiographic image capturing system according to claim 3, wherein the group determining portion determines a second radiation source group to be used in the moving image mode from among the radiation sources; and the radiation source selecting portion selects at least one of the radiation sources from among the second radiation source group determined by the group determining portion in a case where the image capturing mode is the moving image mode.

5. The radiographic image capturing system according to claim 4, wherein the group determining portion determines the first radiation source group and the second radiation source group such that each of the radiation sources belongs to either one of the first radiation source group and the second radiation source group.

6. The radiographic image capturing system according to claim 1, wherein the radiation source selecting portion selects at least one of the radiation sources depending on a positional relationship between a region of interest of a subject as a target to be imaged and each of the radiation sources.

7. The radiographic image capturing system according to claim 6, wherein in the case where the image capturing mode is the still image mode, the radiation source selecting portion selects at least one of the radiation sources, which resides at a position located a short distance with respect to the region of interest.

8. The radiographic image capturing system according to claim 6, wherein in the case where the image capturing mode is the still image mode, the radiation source selecting portion selects at least one of the radiation sources, which resides at a position having a small irradiation angle with respect to the region of interest.

9. The radiographic image capturing system according to claim 1, wherein the radiation source selecting portion selects a cluster of at least two of the radiation sources, as the predetermined surface is viewed in plan.

10. The radiographic image capturing system according to claim 1, wherein the output control portion successively controls the emissions of radiation depending on the still image mode at longer time intervals than a frame interval of the moving image mode.

11. The radiographic image capturing system according to claim 1, further comprising:

a moving mechanism for moving the radiation sources in unison with each other.

12. The radiographic image capturing system according to claim 1, further comprising:

a radiographic image capturing apparatus for converting the radiation emitted respectively from the radiation sources into a radiographic image.

13. A radiographic image capturing method using a radiation output device having a plurality of radiation sources arranged along a predetermined surface, comprising:

selecting at least one of the radiation sources for emitting radiation from among the plurality of radiation sources of the radiation output device, depending on whether an image capturing mode is a still image mode for capturing a radiographic image in a single image capturing event, or a moving image mode for capturing a succession of radiographic images in successive image capturing events.

* * * * *